United States Patent [19]

Nakagami et al.

[11] 4,304,778
[45] * Dec. 8, 1981

[54] 4-AMINOQUINAZOLINE DERIVATIVES HAVING FUNGICIDAL, ANTI-INSECT AND ACARICIDAL PROPERTIES

[75] Inventors: Kazuto Nakagami; Shinji Yokoi, both of Yasu, Japan; Kenji Nishimura, deceased, late of Shiga, Japan, by Yoko Nishimura, legal representative; Shigeki Nagai, Ube, Japan; Takeo Honda, Ube, Japan; Kiroku Oda, Ube, Japan; Katsutoshi Fujii, Ube, Japan; Takashi Kobayashi, Ube, Japan; Mikio Kojima, Ube, Japan

[73] Assignees: Sankyo Company Limited, Tokyo; Ube Industries, Ltd., Ube, both of Japan

[*] Notice: The portion of the term of this patent subsequent to Jul. 22, 1997, has been disclaimed.

[21] Appl. No.: 97,844

[22] Filed: Nov. 27, 1979

[30] Foreign Application Priority Data

Dec. 6, 1978 [JP] Japan ................................ 53-151236

[51] Int. Cl.³ .................... A01N 43/54; C07D 239/94
[52] U.S. Cl. ...................................... 424/251; 544/293
[58] Field of Search ......................... 544/293; 424/251

[56] References Cited

U.S. PATENT DOCUMENTS 4,213,987  7/1980  Nakagami et al. ................... 544/293

FOREIGN PATENT DOCUMENTS

78/3229 10/1979 South Africa .

Primary Examiner—Paul M. Coughlan, Jr.
Attorney, Agent, or Firm—Frishauf, Holtz, Goodman & Woodward

[57] ABSTRACT

4-Aminoquinazoline derivatives of formula (I):

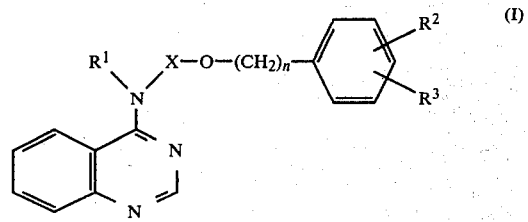

(wherein:
R¹ represents an alkyl group, a cycloalkyl group, an alkenyl group or a benzyl group;
R² and R³ are the same or different and each represents a hydrogen atom, an alkyl group, an alkoxy group or a halogen atom;
X represents a straight or branched chain alkylene group; and
n is 0 or 1)

and salts and hydrates thereof are valuable fungicidal, anti-insect (insect-repellent and insecticidal) and acaricidal compounds and thus can be used to treat or prevent many diseases affecting agricultural and horticultural plants, while, at the same time, having a much lower toxicity to fish than is exhibited by other known compounds.

27 Claims, No Drawings

4-AMINOQUINAZOLINE DERIVATIVES HAVING FUNGICIDAL, ANTI-INSECT AND ACARICIDAL PROPERTIES

BACKGROUND OF THE INVENTION

The present invention relates to a series of new 4-aminoquinazoline derivatives, to their salts and hydrates, to processes for preparing them and to their use in the treatment of various diseases affecting agricultural and horicultural plants.

Certain 4-aminoquinazoline derivatives are disclosed in Japanese Pat. No. 545936 and shown to be effective in the control of phytopathogenic fungi. We have now discovered a class of new 4-aminoquinazoline derivatives which have a broader and better fungicidal activity than do these known compounds against bacteria and fungi parasitic on agricultural and horticultural plants.

Our co-pending US Patent Application Ser. No. 910,117 filed May 30, 1978, U.S. Pat. No. 4,213,987, also discloses a series of fungicidal 4-aminoquinazoline derivatives having excellent fungicidal activity. However, we have surprisingly found that the compounds of the present invention have a significantly lower toxicity to fish than do the compounds of our co-pending Application. As worldwide concern over the pollution of the environment increases, it becomes more and more important that the impact of agricultural chemicals should be limited to the target section of the ecology and, in particular, that agricultural pest-killers should have a low toxicity to animals, plants etc other than the pests which they are designed to kill. Moreover, the low fish toxicity of the compounds of the invention enables these compounds to have a much broader spectrum of use; thus, for example, the compounds of the invention, are especially useful in the treatment of paddy-fields.

BRIEF SUMMARY OF INVENTION

The 4-aminoquinazoline derivatives of the present invention are those compounds of formula (I):

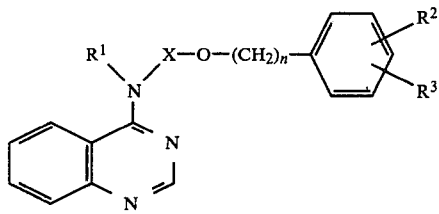

(wherein:
  $R^1$ represents an alkyl group, a cycloalkyl group, an alkenyl group or a benzyl group;
  $R^2$ and $R^3$ are the same or different and each represents a hydrogen atom, an alkyl group, an alkoxy group or a halogen atom;
  X represents a straight or branched chain alkylene group; and
  n is 0 or 1)
and salts and hydrates thereof.

The invention also provides an agricultural or horticultural composition comprising, as active ingredient, one or more of the compounds of the invention in admixture with an agriculturally or horticulturally acceptable carrier or diluent.

The invention still further provides a method of protecting growing plants or seed against bacterial, fungal, insect or mite attack by applying to the seeds, plants or soil one or more of the compounds of the invention.

The invention still further provides processes for preparing the compounds of the invention.

DETAILED DESCRIPTION OF INVENTION

In the compounds of formula (I), when $R^1$ represents an alkyl group, it is preferably a straight or branched chain alkyl group having from 1 to 10 carbon atoms (e.g. a methyl, ethyl, propyl, isopropyl, butyl, isobutyl, sec-butyl, t-butyl, pentyl, hexyl, octyl, 2-ethylhexyl or decyl group), more preferably a straight or branched chain alkyl group having from 1 to 4 carbon atoms.

When $R^1$ represents a cycloalkyl group, it is preferably a cycloalkyl group having from 5 to 7 carbon atoms, more preferably a cyclohexyl group.

When $R^1$ represents a alkenyl group, it is preferably an alkenyl group having from 3 to 6 carbon atoms (e.g. an allyl, 2-butenyl, 2-methylallyl or 2,4-hexadienyl group), more preferably an allyl group.

When either or both of $R^2$ and $R^3$ represents an alkyl group, this is preferably a straight or branched chain alkyl group containing from 1 to 10 carbon atoms (e.g. a methyl, ethyl, propyl, isopropyl, butyl, isobutyl, sec-butyl, t-butyl, pentyl, hexyl, octyl, 2-ethylhexyl or decyl group), more preferably a straight or branched chain alkyl group having from 1 to 4 carbon atoms.

When either or both of $R^2$ and $R^3$ represents an alkoxy group, it is preferably a straight or branched chain alkoxy group having from 1 to 4 carbon atoms (e.g. a methoxy, ethoxy, propoxy, isopropoxy, butoxy, isobutoxy, sec-butoxy or t-butoxy group), more preferably a methoxy group.

When either or both of $R^2$ and $R^3$ represents a halogen atom, it may be a chlorine, bromine, iodine or fluorine atom, more preferably a chlorine atom.

X may represent a straight or branched chain alkylene group, preferably having from 1 to 8 carbon atoms. Examples of such groups include the ethylene, methylmethylene, trimethylene, propylene, tetramethylene, 1,1-dimethylethylene, 1,2-dimethylethylene, 2,2-dimethylethylene, 1-ethylethylene, 2-ethylethylene, pentamethylene, hexamethylene, heptamethylene, octamethylene, 2-ethylhexamethylene or 5-ethylhexamethylene groups. More preferably X represents a straight or branched chain alkylene group having 2 or 3 carbon atoms, most preferably an ethylene group. n, which may be 0 or 1, is preferably 0.

Thus, of the compounds of formula (I), a preferred class of compounds are those in which:
  $R^1$ represents an alkyl group having from 1 to 4 carbon atoms or an allyl group;
  $R^2$ represents an alkyl group having from 1 to 4 carbon atoms,
  $R^3$ represents a hydrogen atom or an alkyl group having from 1 to 10 carbon atoms,
  X represents an ethylene group; and
  n is 0.

Depending upon the nature of the alkylene group represented by X in the compounds of formula (I), these compounds may contain one or more asymmetric carbon atoms and thus may exist in the form of various different optical isomers. The present invention envisages the use of both the individual stereoisomers and physical or racemic mixtures thereof.

Compounds of formula (I) readily form acid addition salts, which are also effective in the control of bacteria, fungi, insects and mites and which also form part of the present invention. Acids which may be used to form such acid addition salts include: inorganic acids, such as hydrochloric acid, hydrobromic acid, nitric acid, sulphuric acid or phosphoric acid; organic carboxylic acid, such as formic acid, oxalic acid or trichloroacetic acid; and organic sulphonic acids, such as methanesulphonic acid, benzenesulphonic acid or the toluenesulphonic acids, particularly p-toluenesulphonic acid. Of these, salts formed with hydrochloric acid are preferred. The salts may be prepared by conventional means, for example by dissolving the compound of formula (I) in a suitable organic solvent, adding the chosen acid and finally evaporating off the solvent. If desired, the salts may be formed as a last step in the preparation of the compounds of the invention, without intermediate isolation of the compound of formula (I) from the reaction mixture.

Compounds of formula (I) may also form hydrates with water, and these hydrates also form part of the present invention. The hydrates may be formed simply by washing the compound of formula (I) with water or by crystallizing the compound from an aqueous organic solvent.

Examples of some of the compounds of the invention are given below. The numbers appended to the compounds in this list will be used to identify them hereafter in the Examples. The melting point or refractive index of each of the compounds in the following list is also given.

1. 4-{N-methyl-N-[2-(2-methylphenoxy)ethyl]amino}-quinazoline—m.p. 94°–96° C.
2. 4-{N-ethyl-N-[2-(2-methylphenoxy)ethyl]amino}-quinazoline—m.p. 85°–87° C.
3. 4-{N-benzyl-N-[2-(2-methylphenoxy)ethyl]amino}-quinazoline—m.p. 100°–102° C.
4. 4-[N-methyl-N-(2-phenoxyethyl)amino]-quinazoline—$n_D^{27}$ 1.6329.
5. 4-[N-ethyl-N-(2-phenoxyethyl)amino]-quinazoline—$n_D^{27}$ 1.6220.
6. 4-{N-[2-(2-methylphenoxy)ethyl]-N-propylamino}-quinazoline—m.p. 57°–60° C.
7. 4-{N-isopropyl-N-[2-(2-methylphenoxy)ethyl]amino}quinazoline—$n_D^{28}$ 1.5990.
8. 4-{N-allyl-N-[2-(2-methylphenoxy)ethyl]amino}-quinazoline—m.p. 81°–84° C.
9. 4-{N-cyclohexyl-N-[2-(2-methylphenoxy)ethyl]amino}quinazoline—$n_D^{20}$ 1.6022.
10. 4-{N-butyl-N-[2-(2-methylphenoxy)ethyl]amino}-quinazoline—m.p. 80°–82° C.
11. 4-{N-[2-(2-chlorophenoxy)ethyl]-N-methylamino}-quinazolone—m.p. 109°–111° C.
12. 4-{N-methyl-N-[2-(2-sec-butylphenoxy)ethyl]amino}quinazoline—$n_D^{22}$ 1.6053.
13. 4-{N-methyl-N-[2-(4-methylbenzyloxy)ethyl]amino}quinazoline—$n_D^{23}$ 1.6136.
14. 4-{N-[2-(4-chlorobenzyloxy)ethyl]-N-methylamino}quinazoline—$n_D^{23}$ 1.6231.
15. 4-{N-[2-(2-isopropylphenoxy)ethyl]-N-methylamino}quinazoline—$n_D^{23}$ 1.6078.
16. 4-{N-[2-(2-methoxyphenoxy)ethyl]-N-methylamino}quinazoline—m.p. 75°–79° C.
17. 4-{N-[2-(2,4-dimethylphenoxy)ethyl]-N-methylamino}-quinazoline—$n_D^{22}$ 1.6134.
18. 4-{N-methyl-N-[2-(4-methylphenoxy)ethyl]amino}-quinazoline—m.p. 70°–72° C.
19. 4-{N-[2-(4-chlorophenoxy)ethyl]-N-methylamino}-quinazoline—m.p. 109°–110° C.
20. 4-{N-methyl-N-[2-(3-methylphenoxy)ethyl]amino}-quinazoline—$n_D^{23}$ 1.6236.
21. 4-{N-[2-(5-isopropyl-2-methylphenoxy)ethyl]-N-methylamino}quinazoline—$n_D^{23}$ 1.6001.
22. 4-{N-[2-(4-chloro-2-methylphenoxy)ethyl]-N-methylamino}quinazoline—m.p. 75°–77° C.
23. 4-{N-[2-(3-chlorophenoxy)ethyl]-N-methylamino}-quinazoline—$n_D^{23}$ 1.6308.
24. 4-{N-[2-(2-isopropylphenoxy)ethyl]-N-propylamino}quinazoline—m.p. 48°–51° C.
25. 4-{N-allyl-N-[2-(2-isopropylphenoxy)ethyl]amino}-quinazoline—m.p. 82°–84° C.
26. 4-{N-allyl-N-[2-(2,4-dimethylphenoxy)ethyl]amino}quinazoline—m.p. 80°–82° C.
27. 4-{N-ethyl-N-[2-(2-isopropylphenoxy)ethyl]amino}quinazoline—m.p. 90°–92° C.
28. 4{N-butyl-N-[2-(2-isopropylphenoxy)ethyl]amino}-quinazoline—m.p. 42°–44° C.
29. 4-{N-isopropyl-N-[2-(2-isopropylphenoxy)ethyl]amino}quinazoline—m.p. 74°–77° C.
30. 4-{N-benzyl-N-[2-(2-isopropylphenoxy)ethyl]amino}quinazoline—m.p. 117°–119° C.
31. 4-{N-cyclohexyl-N-[2-(2-isopropylphenoxy)ethyl]amino}quinazoline—$n_D^{20}$ 1.5976.
32. 4-{N-[2-(2,4-dimethylphenoxy)ethyl]-N-ethylamino}quinazoline—m.p. 80°–83° C.
33. 4-{N-[2-(2,4-dimethylphenoxy)ethyl]-N-propylamino}quinazoline—m.p. 66°–69° C.
34. 4-{N-[2-(2,4-dimethylphenoxy)ethyl]-N-isopropylamino}quinazoline—m.p. 97°–99° C.
35. 4-{N-butyl-N-[2-(2,4-dimethylphenoxy)ethyl]amino}quinazoline—m.p. 50°–52° C.
36. 4-{N-benzyl-N-[2-(2,4-dimethylphenoxy)ethyl]amino}quinazoline—m.p. 115°–118° C.
37. 4-{N-cyclohexyl-N-[2-(2,4-dimethylphenoxy)ethyl]amino}quinazoline—$n_D^{20.5}$ 1.5953.
38. 4-{N-[2-(4-chloro-2-methylphenoxy)ethyl]-N-ethylamino}quinazoline—m.p. 105°–107° C.
39. 4-{N-[2-(4-chloro-2-methylphenoxy)ethyl]-N-propylamino}quinazoline—m.p. 79°–81° C.
40. 4-{N-[2-(4-chloro-2-methylphenoxy)ethyl]-N-isopropylamino}quinazoline—m.p. 94°–96° C.
41. 4-{N-butyl-N-[2-(4-chloro-2-methylphenoxy)ethyl]amino}quinazoline—m.p. 103°–105° C.
42. 4-{N-benzyl-N-[2-(4-chloro-2-methylphenoxy)ethyl]amino}quinazoline—m.p. 109°–111° C.
43. 4-{N-allyl-N-[2-(4-chloro-2-methylphenoxy)ethyl]amino}quinazoline—m.p. 101°–103° C.
44. 4-{N-hexyl-N-[2-(2-isopropylphenoxy)ethyl]amino}quinazoline—m.p. 52°–54° C.
45. 4-{N-[2-(4-chloro-2-methylphenoxy)ethyl]-N-cyclohexylamino}quinazoline—m.p. 89°–92° C.
46. 4-{N-cyclohexyl-N-[2-(2-isopropylphenoxy)ethyl]amino}quinazoline—$n_D^{23.5}$ 1.6028.
47. 4-{N-ethyl-N-[2-(5-isopropyl-2-methylphenoxy)ethyl]amino}quinazoline—$n_D^{23.5}$ 1.5984.
48. 4-{N-[2-(5-isopropyl-2-methylphenoxy)ethyl]-N-propylamino}quinazoline—$n_D^{23.5}$ 1.5959.
49. 4-{N-butyl-N-[2-(5-isopropyl-2-methylphenoxy)ethyl]amino}quinazoline—$n_D^{23.5}$ 1.5848.
50. 4-{N-allyl-N-[2-(5-isopropyl-2-methylphenoxy)ethyl]amino}quinazoline—$n_D^{23.5}$ 1.5911.
51. 4-{N-(2-butenyl)-N-[2-(2-isopropylphenoxy)ethyl]amino}quinazoline—$n_D^{16}$ 1.5939.
52. 4-{N-[2-(2-isopropylphenoxy)ethyl]-N-(2-methylallyl)amino}quinazoline—m.p. 96°–98° C.

53. 4-{N-[2-(2-isopropylphenoxy)ethyl]-N-(3-methyl-2-butenyl)amino}quinazoline—m.p. 86°-88° C.
54. 4-{N-[2-(2-isopropylphenoxy)ethyl]-N-methylamino}quinazoline oxalate—m.p. 107°-109° C.
55. 4-{N-[2-(5-hexyl-2-methylphenoxy)ethyl]-N-methylamino}quinazoline—$n_D^{28.5}$ 1.5836.
56. 4-{N-methyl-N-[2-(2-methyl-5-octylphenoxy)ethyl]amino}quinazoline—$n_D^{28.5}$ 1.5721.
57. 4-{N-[2-(4-hexyl-2-methylphenoxy)ethyl]-N-methylamino}quinazoline—$n_D^{28.5}$ 1.5805.
58. 4-{N-methyl-N-[2-(2-methyl-4-octylphenoxy)ethyl]amino}quinazoline—$n_D^{28.5}$ 1.5731.

Of the compounds listed above, the most preferred compounds, having regard to their biological effectiveness, toxicity and ease of commercialization are compounds Nos. 1, 6, 8, 15, 17, 21, 22, 24, 25, 26, 28, 54, 57 and 58.

Compounds of formula (I) may be prepared by reacting a compound of formula (II) or (III):

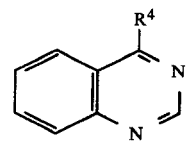 (II)

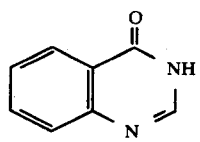 (III)

(in which R$^4$ represents a halogen atom, preferably a chlorine atom, or a mercapto group) with a compound of formula (IV):

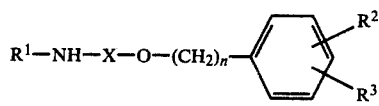 (IV)

(in which R$^1$, R$^2$, R$^3$, X and n are as defined above).

These reactions may be carried out under per se known conditions, preferably in the presence of a solvent and of a base.

The nature of the solvent is not critical, provided that it has no adverse effect upon the reaction. Examples of suitable solvents include: aromatic, aliphatic or alicyclic hydrocarbons, such as benzene, toluene, xylene, methylnaphthalene, petroleum ether, ligroin, hexane or cyclohexane; chlorinated aromatic, aliphatic or alicyclic hydrocarbons, such as chlorobenzene, the dichlorobenzenes, methylene chloride, chloroform, dichloroethane or trichloroethylene; ethers, such as diethyl ether, ethylene glycol dimethyl ether, tetrahydrofuran or dioxan; ketones, such as acetone or methyl ether ketone; and alcohols, such as methanol, ethanol or ethylene glycol. Any one of these solvents may be used alone or a mixture of two or more may be employed. It is also possible to use a mixture of any one or more of these solvents with water.

Examples of suitable bases include: organic bases, such as triethylamine, pyridine and N,N-diethylaniline; and inorganic bases, such as sodium hydroxide, potasium hydroxide, sodium carbonate and potassium carbonate.

The reaction temperature is not critical and the reaction is, for convenience, therefore usually carried out at a temperature within the range from ambient temperature to the reflux temperature of the solvent employed. We prefer that the reaction should be performed with heating, in order to reduce the reaction period.

When the reaction is complete, the desired compound may be separated from the reaction mixture using known techniques and then, if desired, purified by conventional methods, such as recrystallization or chromatography.

Acid addition salts may readily be prepared by introducing the chosen acid into the reaction mixture before evaporating off the solvent employed for the reaction. Similarly, hydrates may be obtained by recrystallizing the desired compound from a solvent containing.

The compounds of the invention have excellent activity against a wide range of diseases affecting agricultural and horticultural plants. Thus, for example, they will protect rice plants against blast, brown spot, sheath blight and bacterial leaf blight; they will protect tomatoes against late and early blight; and they will protect cucumbers against anthracnose, downy mildew and powdery mildew. They also control phytoparastic soil fungi and algal fungi, which adversely affect the germination of rice plants.

Moreover, the compounds of the invention have a powerful controlling influence on insects and mites parasitic on plants and, furthermore, they inhibit ingestion by the fourth to final instar larvae of Lepidoptera, such as the cabbage armyworm and the tobacco cutworm. The compounds of the invention are thus also useful as insecticides, insect repellents and acaricides.

The compounds of the invention may be formulated as preparations of the type commonly used as agricultural fungicides, insecticides or acaricides, for example as powdery dusts, coarse dusts, fine granules, coarse granules, wettable powders, emulsifiable concentrates, aqueous liquids, water-soluble powders or oil suspensions, by mixing them with a carrier and, if required, another auxiliary agent. The carrier employed may be natural or synthetic and organic or inorganic; it is mixed with the active ingredient, the compound of formula (I), to assist that active ingredient to reach the plant, seed, soil or other material to be treated, and to make it easier to store, transport or handle the active ingredient. Suitable solid carriers are: inorganic substances, such as clays (examples of which are kaolinite, montmorillonite and attapulgite), talc, mica, pyrophyllite, pumice, vermiculite, gypsum, calcium carbonate, dolomite, diatomaceous earth, magnesium carbonate, apatite, zeolite, silicic anhydride and synthetic calcium silicate; vegetable organic substances, such as soybean meal, tobacco powder, walnut powder, wheat flour, woodmeal, starch and crystalline cellulose; synthetic or natural high molecular weight polymers, such as cumarone resins, petroleum resins, alkyd resins, polyvinyl chloride, polyalkylene glycols, ketone resins, ester gums, copal gums and dammar gums; waxes, such as carnauba wax and beeswax; or urea. Examples of suitable liquid carriers are: paraffinic or naphthenic hydrocarbons, such as kerosine, mineral oil, spindle oil and white oi; aromatic hydrocarbons, such as benzene, toluene, xylene, ethylbenzene, cumene and methylnaphthalene; chlorinated hydrocarbons, such as carbon tetrachloride, chloroform, trichloroethylene, monochlorobenzene and o- chlorotoluene; ethers, such as dioxan and tetrahydrofuran; ketones, such as acetone, methyl ethyl ketone, diisobutyl ketone, cyclohexanone, acetophenone and isophorone; esters, such as ethyl acetate, amyl acetate, ethylene glycol acetate, diethylene glycol acetate, dibutyl maleate and diethyl succinate; alcohols, such as methanol, hexanol, ethylene glycol, diethylene glycol, cyclohexanol and benzyl alcohol; ether alcohols, such as ethylene glycol monoethyl ether, ethylene glycol monophenyl ether, diethylene glycol monoethyl ether and diethylene glycol monobutyl ether; other polar organic solvents, such as dimethylformamide or dimethyl sulphoxide; and water.

The fungicidal, insecticidal and acaricidal compositions of the present invention may also contain surface active agents to emulsify, disperse, wet, spread, bind, control disintegration improve fluidity or rust-proof the composition or to stabilize the active compound. Although any of the conventional classes of surface active agent, be they non-ionic, anionic, cationic or amphoteric, may be employed, we prefer to employ non-ionic and/or anionic surface active agents. Examples of suitable non-ionic surface active agents are: the polymerization adducts of ethylene glycol with higher alcohols, such as lauryl alcohol, stearyl alcohol and oleyl alcohol; the polymerization adducts of ethylene oxide with alkylphenols, such as isooctyl phenol and nonylphenol; the polymerization adducts of ethylene glycol with alkylnaphthols, such as butylnaphthol or octylnaphthol; the polymerization adducts of ethylene oxide with higher fatty acids, such as palmitic acid, stearic acid or oleic acid; the polymerization adducts of ethylene oxide with mono- or dialkylphosphoric acids, such as stearylphosphoric acid or dilaurylphosphoric acid; the polymerization adducts of ethylene oxide with amines, such as dodecylamine; the polymerization adducts of ethylene oxide with higher fatty acid amides, such as stearamide; the polymerization adducts of ethylene oxide with higher fatty acid esters of polyhydric alcohols, such as sorbitan; higher fatty acid esters of polyhydric alcohols; and the polymerization adducts of ethylene oxide with propylene oxide. Examples of suitable anionic surface active agents are: alkyl sulphate salts, such as sodium lauryl sulphate or oleyl sulphate amine salt; alkyl sulphonate salts, such as sodium dioctyl sulphosuccinate or sodium 2-ethylhexene sulphonate; and aryl sulphonate salts, such as sodium isopropylnaphthalene sulphonate, sodium methylenebisnaphthalene sulphonate, sodium ligninsulphonate or sodium dodecylbenzene sulphonate.

Moreover, the compositions of the present invention may be used in combination with high molecular weight compounds or other auxiliary agents, such as casein, gelatin, albumin, glue, sodium alginate, carboxymethylcellulose, methylcellulose, hydroxyethylcellulose or polyvinyl alcohol, in order to improve the properties and/or to increase the biological effect of the compositions.

The above-mentioned carriers and their auxiliary agents may be used alone or in any desired combination, depending upon the type of preparation, the application and other factors.

In general, the composition of the invention may contain the active compound of formula (I) in an amount of from 0.1 to 99% by weight, based on the composition; however, the exact amount of active compound chosen will depend on the physical nature of the compound itself and on the type of composition into which it is to be incorporated.

Thus, for example, dusts may conveniently contain from 1 to 25% by weight of the active compound of formula (I), the remainder being a solid carrier.

Wettable powders may conveniently contain, for example, from 25 to 90% by weight of the active compound of formula (I), the remainder being a solid carrier and a dispersing and wetting agent, if required, together with a protective colloidal agent, a thixotropic agent and an anti-foaming agent.

Granules may conveniently contain from 1 to 35% by weight of the active compound of formula (I), a major portion of the remainder being a solid carrier. The active compound is homogeneously admixed with the solid carrier or adhered or adsorbed onto the carrier surface; the size of each granule is preferably from 0.2 to 1.5 mm.

Emulsifiable concentrates may conveniently contain, for example, from 5 to 50% by weight of the active compound of formula (I) and from 5 to 20% by weight of an emulsifying agent, the remainder being a liquid carrier, together with a corrosion inhibitor, if required.

The compositions of the invention, which are formulated into the various types of preparation described above, may be applied to a paddy or upland (dry) field in an amount of from 1 to 5000 g, more preferably from 10 to 1000 g, of the active compound of formula (I) per 10 ares for pre- or post- emergence fungicidal, antiinsect and acaricidal activity. The composition may be applied by foliage spraying, soil drenching or spraying onto irrigation water. The compositions of the invention, when employed for seed disinfection or coating, effectively control soil-borne or seed infectious diseases by coating seeds in an amount of from 0.1 to 2%, preferably from 0.2 to 0.5%, by weight of the active ingredient, based on the weight of the seed.

The compositions of the invention may be blended with other fungicides and/or insecticides and/or acaricides for a broader fungicidal, anti-insect or acaricidal spectrum and, in some cases, a synergistic effect may be observed.

Examples of other fungicides which may be employed in combination with the compounds of the present invention are: carbamate-type fungicides, such as 3,3'-ethylenebis(tetrahydro-4,6-dimethyl-2H-1,3,5-thiadiazine-2-thione), zinc or manganese ethylenebisdithiocarbamate, bis(dimethyldithiocarbamoyl)disulphide, zinc propylenebisdithiocarbamate, bis(dimethyldithiocarbamoyl) ethylene diamine, nickel dimethyldithiocarbamate, methyl 1-(butylcarbamoyl)-2-benzimidazolcarbamate, 1,2-bis(3-methoxycarbonyl-2-thioureido)benzene, 1-isopropylcarbamoyl-3-(3,5-dichlorophenyl)hydantoin potassium N-hydroxymethyl-N-methyldithiocarbamate or 5-methyl-10-butoxycarbonylamino-10,11-dehydrodibenzo[b,f]azepine; pyridine-type fungicides, such as zinc bis[1-hydroxy-2(1H)pyridinethionate] and sodium 2-pyridinethiol-1-oxide; phosphorus-containing fungicides, such as O,O-diisopropyl-S-benzylphosphorothioate and O-ethyl-S,S-diphenyldithiophosphate; phthalimide-type fungicides, such as N-(2,6-diethylphenyl)phthalimide and N-(2,6-diethylphenyl)-4-methylphthalimide; dicarboximide-type fungicides, such as N-trichloromethylthio-4-cyclohexene-1,2-dicarboximide and N-tetrachloroethylthio-4-cyclohexene-1,2-dicarboximide; oxazine-type fungicides, such as 5,6-dihydro-2-methyl-1,4-oxazine-3-carboxanilide-4,4-dioxide and 5,6-dihydro-2-methyl- 1,4-oxazine-3-carboxanilide; naphthoquinone-type fungicides, such as 2,3-dichloro-1,4-naphthoquinone and 2-oxy-3-chloro-1,4-naphthoquinone copper sulphate adduct; and other fungicides, such as pentachloronitrobenzene, 1,4-dichloro-2,5-dimethoxybenzene, 5-methyl-s-triazole[3,4-b]benzthiazole, 2-(thiocyanomethylthio)-benzthiazole, 3-hydroxy-5-methylisoxazole, N-(2,3-dichlorophenyl)tetrachlorophthalamic acid, 5-ethoxy-3-trichloromethyl-1,2,4-thiadiazole, 2,4,6-trichloro-6-(o-chloroanilino)-1,3,5-triazine, 2,3-dicyano-1,4-dithioanthraquinone, copper 8-quinolate, polyoxin, validamycin, cycloheximide, iron methanearsonate, tetrachloroisophthalonitrile, 2-(1-methylpropyl)-4,6-dinitrophenol β,β-dimethylacrylate, triphenyltin hydroxide, phytomycin, kasugamycin, blasticidin S and 4,5,6,7-tetrachlorophthalide. However, the nature of such additional fungicides is not critical and, as is well-known in the art, provided there is no adverse inter-reaction, any other known fungicides may be employed.

The compounds of the invention may also be employed in admixture with various other insecticides. Suitable insecticides include: phosphorus-containing insecticides, such as O,O-diethyl O-(2-isopropyl-4-methyl-6-pyrimidinyl)phosphorothioate, O,O-diethyl S-[2-(ethylthio)ethyl]phosphorodithioate, O,O-dimethyl O-(3-methyl-4-nitrophenyl)thiophosphate, O,O-dimethyl S-(N-methylcarbamoylmethyl)phosphorodithioate, O,O-dimethyl S-(N-methyl-N-formylcarbamoylmethyl)phosphorodithioate, O,O-dimethyl S-[2-(ethylthio)ethyl]phosphorodithioate, O,O-diethyl S-[2-(ethylthio)ethyl]phosphorodithioate, O,O-dimethyl 1-hydroxy-2,2,2-trichloroethylphosphonate, O,O-diethyl O-(5-phenyl-3-isoxazolyl)phosphorothioate, methyl (4-bromo-2,5-dichlorophenyl)phenylphosphonothioate, O,O-dimethyl O-(3-methyl-4-methylmercaptophenyl)thiophosphate, O-ethyl-O-p-cyanophenyl phenylphosphonothioate, O,O-diethyl S-(1,2-dicarboethoxyethyl)phosphorodithioate, 2-chloro-1-(2,4,5-trichlorophenyl)vinyldimethyl phosphate, 2-chloro-1-(2,4-dichlorophenyl)vinyldimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenylacetate, O,O-dimethyl phosphorodithioate, S-[(6-chloro-2-oxo-3-benzoxazolinyl)methyl]O,O-diethyl-phosphorodithioate, 4-mercaptothiophenyl dipropylphosphate, 2-chloro-1-(2,4-dichlorophenyl)vinyl diethylphosphate, O,O-diethyl O-(3-oxo-2-phenyl-2H-pyridazin-6-yl)phosphorothioate, O,O-dimethyl S-(1-methyl-2-ethylsulphinyl)ethyl phosphorothiolate, O,O-dimethyl S-phthalimidomethyl phosphorodithioate, dimethylmethylcarbamoylethylthioethyl thiophosphorothiolate, O,O-diethyl S-(N-ethoxycarbonyl-N-methylcarbamoylmethyl)phosphorodithioate, O,O-dimethyl S-[2-methoxy-1,3,4-thiadiazol-5(4H)-onyl-(4)-methyl]dithiophosphate, 2-methoxy-4H-1,3,2-benzodioxaphosphorin 2-sulphide, O,O-diethyl O-(3,5,6-trichloro-2-pyridyl)phosphorothioate, O-ethyl-O-2,4-dichlorophenyl thionobenzenephosphate S-[4,6-diamino-s-triazin-2-ylmethyl]-O,O-dimethyl phosphorodithioate, O-ethyl O-p-nitrophenyl phenylphosphorothioate, O,S-dimethyl-N-acetyl phosphoroamidothioate, 2-diethylamino-6-methylpyrimidin-4-yl diethylphosphorothioate, O,O-diethyl O-p-(methylsulphinyl)-phenyl phosphorothioate, O-ethyl S-propyl O-(2,4-dichlorophenyl)phosphorodithioate and cis-3-(dimethoxyphosphinoxy)-N-methyl-cis-crotonamide; carbamate-type insecticides, such as 1-naphthyl, N-methyl-carbamate, S-methyl-N-[methylcarbamoyloxy]thioacetoimidate, m-tolyl methylcarbamate, 3,4-xylyl methylcarbamate, 3,5-xylyl methylcarbamate, 2-sec-butylphenyl, N-methylcarbamate, 2,3-dihydro-2,2-dimethyl-7-benzofuranylmethylcarbamate, 2-isopropoxyphenyl-N-methylcarbamate, 1,3-bis(carbamoylthio)-2-(N,N-dimethylamino)-propane hydrochloride and 2-diethylamino-6-methylpyrimidin-4-yl dimethylcarbamate, and other insecticides such as N,N-dimethyl-N'-(2-methyl-4-chlorophenyl)formamidine hydrochloride, nicotine sulphate, silbemycin, 6-methyl-2,3-quinoxalinedithiocyclic S,S-dithiocarbonate, 2,4-dinitro-6-sec-butylphenyl dimethylacrylate, 1,1-bis-(p-chlorophenyl)-2,2,2-trichloroethanol, 2-(p-t-butylphenoxy)isopropyl-2'-chloroethyl sulphite, azoxybenzene, di-(p-chlorophenyl)cyclopropyl carbinol, isopropyl 4,4'-dichlorobenzylate, ethyl 4,4'-dichlorobenzylate and machine oil.

The compositions of the invention may also be used together with control agents effective against rice blast, helminthosporium leaf spot, bacterial leaf blight, rice stem borers, planthoppers and/or leafhoppers, to save the labour involved in separate applications. A combination of one or more of the additional agents described above with the composition of the invention may be employed, depending upon the disease and/or insect and/or mite to be controlled and the form of the composition to be employed. We particularly prefer to employ the composition of the invention in the form of a dust, in the form of fine granules for controlling rice plant diseases or for soil treatment.

The invention is further illustrated by the following Examples, of which Examples 1 and 2 illustrate the preparation of compounds of the invention, Examples 3 to 5 illustrate the preparation of compositions according to the invention and the remaining Examples illustrate the biological activity of the compounds. In these Examples, all parts are by weight.

EXAMPLE 1

4-{N-ethyl-N-[2-(2-methylphenoxy)ethyl]amino}-quinazoline (Compound No. 2)

To a solution of 2.5 g (0.015 mole) of 4-chloroquinazoline in toluene were added 2.7 g (0.015 mole) of N-ethyl-2-(2-methylphenoxy)ethylamine and 1.5 g (0.015 mole) of triethylamine. The mixture was then refluxed, with stirring, for 5.5 hours. After completion of the reaction, the toluene was removed from the reaction mixture by evaporation under reduced pressure. Water was then added to the residue and the mixture was extracted with chloroform and the extract was dried. The chloroform was removed by evaporation and the crystals which separated out were recrystallized from isopropanol, giving 2.5 g (54%) of the desired Compound No. 2, in the form of colourless prisms melting at 85°–87° C.

Elemental Analysis: Calculated: C,74.24%; H,6.89%; N,13.67%. Found: C,74.20%; H,7.00%; N,13.20%.

EXAMPLE 2

4-[N-methyl-N-(2-phenoxyethyl)amino]quinazoline (Compound No. 4)

To a solution of 2.5 g (0.015 mole) of 4-chloroquinazoline in benzene were added 2.3 g (0.015 mole) of N-methyl-N-phenoxyethylamine and 1.5 g (0.015 mole) of triethylamine. The mixture was then refluxed, with stirring, for 7 hours. After completion of the reaction, the benzene was removed by evaporation. Water was added to the residue and the mixture was extracted with chloroform and the extract was dried. The chloroform was removed by evaporation and the resulting oil was purified by column chromatography through silica gel (eluted with a 1:1 by volume mixture of benzene and ethyl acetate) to give 3.7 g (88%) of the desired Compound No. 4 in the form of a pale yellow liquid having a refractive index $n_D^{27}$ 1.6329.

Following the same general procedures as described in the above Examples, Compounds No. 1, 3 and 5–58 were also prepared, their properties are as shown in the foregoing list.

EXAMPLE 3

Dust 5 parts of Compound No. 1, 50 parts of talc and 45 parts of kaolin were uniformly mixed to form a dust.

EXAMPLE 4

Wettable Powder 50 parts of Compound No. 21, 29 parts of clay, 10 parts of diatomaceous earth, 5 parts of white carbon, 3 parts of sodium ligninsulphonate, 2 parts of "Newcol" 1106 (a trade name of Nihon Nyukazai K.K., Japan) and 1 part of polyvinyl alcohol, were uniformly mixed in a mixer and then pulverized three times by a hammer mill to give a wettable powder.

EXAMPLE 5

Granules 70 parts of Compound No. 8 were finely pulverized, and then 30 parts of clay were added thereto and then mixed in a mixer to form a premix. 10 parts of this premix were uniformly mixed in a mixer with 60 parts of clay and 30 parts of bentonite. The mixture was then kneaded with a suitable amount of water in a kneader, extruded through a screen with holes having a diameter of 0.8 mm and dried in a draught drier at 50° C. The product thus formed was adjusted by a sifter to form granules.

In the following Examples, wettable powders prepared according to the procedures of Example 4 were used, each powder containing 50% by weight of the active compound of this invention.

EXAMPLE 6

Effect against rice blast

Rice plant seedlings (variety, Nohrin No. 20) at the 4 to 5 leaf stage were sprayed with a test preparation (produced by diluting a wettable powder containing the compound shown in Table 1 to a concentration of 500 ppm) in a total amount of 30 ml per 2 pots. Each pot contained 5 plants. After 3 days, rice blast fungi were inoculated onto the host plants by spraying a spore suspension of *Piricularia oryzae* onto them, and the host plants were kept in a room for 48 hours at 20°–22° C. and 100% relative humidity. The host plants were then placed in a greenhouse at 24°–26° C., and, after a further 3 days, the number of disease spots on the upper two leaves of each of the host plants was counted. Each test was conducted in triplicate and the damage is indicated in Table 1 by the mean number of disease spots per leaf. None of the active compounds exhibited phytotoxicity.

TABLE 1

| Test Compound No. | No. of disease spots per leaf |
|---|---|
| 13 | 2.9 |
| 14 | 1.5 |
| 15 | 3.0 |
| 17 | 2.4 |
| 18 | 2.6 |
| 44 | 3.1 |
| 56 | 3.2 |

EXAMPLE 7

Effect on late blight in tomatoes

Groups of tomatoes (variety Shinfukuju) at the 5 to 6 leaf stage, 2 plants per pot, were sprayed with 20 ml per pot of an aqueous suspension containing 500 ppm of one of the active compounds shown in the following Table 2. After air-drying the plants, a spore suspension of the pathogenic microorganism *Phytophthora infestans* was sprayed onto each plant and the plants were kept for 24 hours in a wet room at 20° C. and more than 95% humidity. The pots were then kept in a greenhouse at 25° C. and, after 5 days, the diseased area of the upper three leaves of each plant was measured. Two pots were used for each test and the average diseased area per leaf was calculated for each of the active compounds of the invention. The results are given in Table 2. None of the compounds of the invention exhibited any phytotoxicity.

TABLE 2

| Test Compound No. | Diseased area (%) |
|---|---|
| 1 | 0 |
| 2 | 3 |
| 3 | 11 |
| 6 | 0 |
| 8 | 5 |
| 9 | 13 |
| 11 | 3 |
| 12 | 15 |
| 15 | 0 |
| 16 | 13 |
| 17 | 9 |
| 18 | 16 |
| 21 | 12 |
| 22 | 15 |
| 25 | 0 |
| 26 | 3 |
| 32 | 5 |
| 34 | 0 |
| 38 | 13 |
| 39 | 9 |
| 43 | 11 |
| 46 | 0 |
| 51 | 0 |
| 52 | 13 |
| 53 | 0 |
| 54 | 0 |
| 58 | 10 |

EXAMPLE 8

Effect on early blight in tomatoes

Groups of tomato plants (variety Shinfukuju) were planted, two per pot, in a series of Wagner pots (diameter 12 cm) and used for the following test when at the 5 to 6 leaf stage. Each pot was treated with 30 ml of an aqueous suspension containing 500 ppm of one of the active compounds shown in Table 3, applied to the plants by spraying over their stems and leaves. After air-drying the plants, a spore suspension of the pathogenic microorganism *Alternalia solani* was sprayed over each plant, and the plants were kept in a wet room for 24 hours at 20°–22° C. and 100% relative humidity. The pots were then placed in a greenhouse for 3 days. All leaves were then examined for signs of the disease and the number of disease spots per leaf was calculated, using three pots for each compound. The results are given in Table 3. None of the active compounds of the invention exhibited any phytotoxicity.

TABLE 3

| Test Compound No. | No. of disease spots per leaf |
| --- | --- |
| 1 | 8 |
| 2 | 16 |
| 9 | 15 |
| 10 | 4 |
| 25 | 15 |
| 31 | 13 |
| 34 | 15 |
| 51 | 4 |

EXAMPLE 9

Effect on anthracnose in cucumbers

Groups of cucumber plants (variety Sagamihanshiro) were planted, two per pot, in a series of Wagner pots (diameter 12 cm) and were used as host plants when the first leaf was fully grown and open. Each test group of three pots was treated with one of the active compounds shown in Table 4 by spraying an aqueous suspension containing 500 ppm of the active compound onto the plants at the rate of 30 ml per 3 pots. After air-drying the plants, a spore suspension of the pathogenic microorganism *Colletotrichum lagenarium* was sprayed onto the plants and the plants were kept in a wet room for 24 hours at 20°–22° C. and 100% relative humidity. The pots were then placed in a greenhouse at 26° C. and, seven days after the spore suspension had been sprayed on, the percentage diseased area of the cotyledon and the first leaf was calculated. The results are given in Table 4. None of the active compounds of the invention exhibited any phytotoxicity.

TABLE 4

| Test Compound No. | Diseased area (%) |
| --- | --- |
| 1 | 0 |
| 2 | 0 |
| 21 | 0 |
| 22 | 0 |
| 25 | 8 |
| 26 | 0 |
| 32 | 8 |
| 51 | 0 |
| 52 | 8 |

EXAMPLE 10

Effect on powdery mildew in cucumbers

Cucumber seedlings (variety Sagamihanshiro), planted two per 12 cm diameter pot, were used as host plants at the stage when the first leaf was fully grown and open. Each test group of three pots was treated with one of the active compounds shown in Table 5 by spraying an aqueous suspension containing 500 ppm of the active compound onto the plants at the rate of 20 ml per 3 pots. After air-drying the plants, the host plants were inoculated with the microorganism *Sphaerotheca fuliginea* by brushing already infected cucumber leaves with a small brush and letting the microorganism fall onto the host plants. The inoculated plants were kept in a greenhouse at 24°–26° C. for 10 days. At the end of this time, the percentage diseased area was measured. Three pots were used for each test and the results are given in Table 5. None of the active compounds of the invention exhibited any phytotoxicity.

TABLE 5

| Test Cpd. No. | Diseased area (%) | Test Cpd. No. | Diseased area (%) |
| --- | --- | --- | --- |
| 1 | 0 | 27 | 0 |
| 2 | 0 | 28 | 0 |
| 3 | 0 | 32 | 0 |
| 5 | 6 | 33 | 0 |
| 6 | 0 | 34 | 10 |
| 7 | 0 | 35 | 0 |
| 8 | 0 | 36 | 0 |
| 10 | 0 | 38 | 0 |
| 15 | 0 | 39 | 0 |
| 17 | 0 | 40 | 0 |
| 18 | 8 | 43 | 0 |
| 21 | 0 | 47 | 0 |
| 22 | 0 | 48 | 0 |
| 24 | 0 | 49 | 0 |
| 25 | 0 | 51 | 0 |
| 26 | 0 | 52 | 0 |

EXAMPLE 11

Repellent action against the third instar larvae of the tobacco cutworm

Cabbage leaves were dipped for 30 seconds in an aqueous suspension containing 500 ppm of one of the active compounds shown in Table 6. After air-drying, each leaf was placed into a plastic receptacle having a diameter of 8 cm and the third instar larvae (10 per receptacle) of the tobacco cutworm were released onto the leaves. After 72 hours, the extent of ingestion of the leaves was measured, using two receptacles for each test compound. The results are shown in Table 6, using the following notation (which is also employed, with the same meaning, in following Table 9):

− = no ingestion
± = very little ingestion
+ = some ingestion
+ + = considerable ingestion

TABLE 6

| Test Compound No. | Extent of ingestion |
| --- | --- |
| 15 | ± to + |
| 17 | + |
| 19 | + |
| 21 | + |
| 22 | ± to + |
| 26 | ± to + |
| 38 | ± |
| 41 | ± to + |
| 43 | + |
| 47 | ± to + |
| 57 | ± |
| 58 | ± to + |
| Control (none) | + + |

EXAMPLE 12

Acaricidal effect on two-spotted spider mites

A wettable powder prepared as described in Example 4 was diluted to the concentrations shown in Table 7 and 0.01% of a spreader was added. Cowpea leaves (*Vigna sinensis*) bearing two-spotted spider mites (*Tetranychus urticae*) were dipped for 10 seconds in the suspension. After air-drying the leaves, they were placed in receptacles and left there at 25° C. After 72 hours, the mortality rate of the mites was determined. After 14 days, the mortality of the eggs (i.e. the presence or absence of hatching) was determined. About 50 mites were used for each test. The results were evaluated according to the evaluation table shown in Table 7. The results are reported in Table 8.

TABLE 7

| Acaricidal effect | Mortality of adult mites or eggs (%) at | | |
|---|---|---|---|
| | 1000ppm | 300ppm | 100ppm |
| 0 | 29-0 | 29-0 | 29-0 |
| 1 | 79-30 | 29-0 | 29-0 |
| 2 | 99-80 | 79-30 | 29-0 |
| 3 | 100 | 99-80 | 79-30 |
| ≧4 | 100 | 100 | 100-80 |

TABLE 8

| Test Compound No. | Acaricidal Effect | |
|---|---|---|
| | Adults | Eggs |
| 4 | — | ≧4 |
| 13 | 3 | — |
| 14 | 3 | — |
| 18 | 3 | — |
| 21 | ≧4 | ≧4 |
| 32 | 3 | — |
| 47 | 3 | — |
| 48 | 3 | — |
| 50 | 3 | — |
| 54 | 3 | — |
| 57 | ≧4 | ≧4 |
| 58 | 3 | — |

EXAMPLE 13

Repellent and emergence-inhibition effect on the final instar larvae of diamondback moths Leaves of the Japanese radish (*Raphanus sativus*) were dipped for 30 seconds into a liquid containing 500 ppm of one of the compounds shown in Table 9. After air-drying the leaves, each leaf was placed into a plastic icecream cup (diameter 8 cm) and 15 final instar larvae of the diamondback moth (*Plutella xylostella*) were placed into each cup. The extent of ingestion and the emergence-inhibition rate after 72 hours were determined and the results are shown in Table 9. Each test was conducted in duplicate and the results were averaged.

TABLE 9

| Test Compound No. | Emergence-inhibition rate (%) | Extent of ingestion |
|---|---|---|
| 15 | 60 | ± |
| 17 | 50 | ± to + |
| 19 | 80 | ± |
| 21 | 90 | ± |
| 22 | 80 | ± |
| 26 | 80 | ± to + |
| 29 | 60 | ± to + |
| 37 | 60 | ± to + |
| 38 | 100 | − to ± |
| 41 | 90 | ± |
| 42 | 60 | ± to + |
| 43 | 70 | ± |
| 47 | 90 | ± |
| 57 | 100 | − to ± |
| 58 | 85 | ± |

EXAMPLE 14

Effect on cockroach larvae 1 mg or 0.5 mg of each in turn of the compounds shown in Table 10 was applied to form a dry film on the bottom of a 20 ml glass bottle (inner diameter 23 mm, height 44 mm). 10 cockroach larvae, 4 days after hatching, were put into each bottle and a cap was then applied. The bottles were maintained at 25° C. and the mortality rate was determined after 24 hours. Each test was conducted in duplicate and the results are shown in Table 10.

TABLE 10

| Test Compound No. | Mortality rate (%) | |
|---|---|---|
| | 1mg test cpd/10 cockroaches/bottle | 0.5mg test cpd/10 cockroaches/bottle |
| 2 | 100 | 90 |
| 4 | 100 | 85 |
| 12 | 100 | 90 |
| 13 | 100 | 80 |
| 15 | 100 | 80 |
| 17 | 100 | 90 |
| 18 | 100 | 90 |
| 19 | 100 | 85 |
| 20 | 100 | 90 |
| 21 | 100 | 90 |
| 22 | 100 | 80 |
| 23 | 100 | 85 |
| 25 | 100 | 85 |
| 26 | 100 | 90 |
| 32 | 100 | 85 |
| 33 | 100 | 90 |
| 38 | 100 | 90 |
| 39 | 100 | 85 |
| 41 | 100 | 85 |
| 43 | 100 | 90 |
| 47 | 100 | 85 |
| 57 | 100 | 90 |
| 58 | 100 | 90 |

EXAMPLE 15

Effect on the cotton aphid

Cucumbers (variety "Tokiwa Hikari No. 3, Type P") were transplanted into a plastic greenhouse on September 12. Using a shoulder sprayer, a liquid containing 600 ppm of one of the compounds shown in Table 11 was sprayed on the surface and reverse side of the leaves on Sept. 25, Oct. 9, 16, 23 and 30. On Nov. 9, the effect on the cotton aphid (*Aphis gossyppi*) was investigated, sampling 25–30 leaves at random from each test area and calculating the number of colonies on each leaf; there were generally 50–100 aphids per colony. The results are shown as the number of colonies per leaf in Table 11, which also gives the results for a test area where no compound of the invention was applied.

TABLE 11

| Test Compound No. | No. of colonies per leaf |
|---|---|
| 21 | 1.0 |
| 22 | 1.1 |
| 58 | 0.5 |
| Control (none) | 8.7 |

EXAMPLE 16

Toxicity to guppies

In this example the toxicity of the compounds of the invention towards guppies was estimated and is compared with that of corresponding compounds as disclosed and claimed in our co-pending U.S. Application No. 910,117 filed May 30, 1978. The $LC_{50}$ was determined after 48 hours and the toxicity to guppies was classified into the rankings (i), (ii) and (iii) according to the following classification scheme:

(i): all fish alive at 10 ppm;
(ii): all fish dead at 10 ppm but alive at 0.5 ppm;
(iii): all fish dead at 0.5 ppm.

The results are shown in Table 12.

The compounds of our earlier Application are identified as follows:
Compound A=4-{N-[2-(2-methylphenoxy)ethyl]amino}quinazoline;
Compound B=4-{N-[2-(2-isopropylphenoxy)ethyl]amino}quinazoline;
Compound C=4-{N-[2-(2,4-dimethylphenoxy)ethyl]amino}quinazoline;
Compound D=4-{N-[2-(4-chloro-2-methylphenoxy)ethyl]amino}quinazoline.

In the Table the compounds of the invention are listed in groups and, in each group, X, n, $R^2$ and $R^3$ are the same and included in the group is the corresponding compound of our earlier Application in which $R^1$ represents a hydrogen atom.

TABLE 12

| Test Compound No. | Toxicity ranking |
|---|---|
| 1 | ii |
| 2 | ii |
| 3 | i |
| 7 | ii |
| 8 | ii |
| A | iii |
| 15 | ii |
| 52 | i |
| 53 | ii |
| B | iii |
| 17 | ii |
| 35 | ii |
| 36 | ii |
| C | iii |
| 39 | ii |
| 40 | i |
| D | iii |

We claim:

1. Compounds of formula (I):

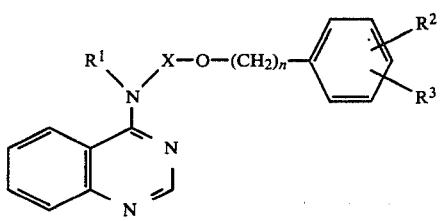

wherein:
$R^1$ represents an alkyl group, a cycloalkyl group, an alkenyl group or a benzyl group;
$R^2$ and $R^3$ are the same or different and each represents a hydrogen atom, an alkyl group, an alkoxy group or a halogen atom;
X represents an alkylene group; and
n represents 0 or 1; and salts and hydrates thereof.

2. Compounds as claimed in claim 1, wherein $R^1$ represents an alkyl group having from 1 to 10 carbon atoms, a cycloalkyl group having from 5 to 7 carbon atoms, an alkenyl group having from 3 to 6 carbon atoms or a benzyl group.

3. Compounds as claimed in claim 2, wherein $R^1$ represents an alkyl group having from 1 to 4 carbon atoms, a cyclohexyl group, an allyl group or a benzyl group.

4. Compounds as claimed in claim 3, wherein $R^1$ represents an alkyl group having from 1 to 4 carbon atoms or an allyl group.

5. Compounds as claimed in claim 1, wherein X represents an alkylene group having from 1 to 8 carbon atoms.

6. Compounds as claimed in claim 5, wherein X represents an alkylene group having 2 or 3 carbon atoms.

7. Compounds as claimed in claim 6, wherein X represents an ethylene group.

8. Compounds as claimed in claim 1, wherein $R^2$ and $R^3$ are the same or different and each represents a hydrogen atom, an alkyl group having from 1 to 10 carbon atoms, an alkoxy group having from 1 to 4 carbon atoms or a halogen atom.

9. Compounds as claimed in claim 8, wherein $R^2$ and $R^3$ are the same or different and each represents a hydrogen atom, an alkyl group having from 1 to 10 carbon atoms, a methoxy group or an chlorine atom.

10. Compounds as claimed in claim 9, wherein $R^2$ represents an alkyl group having from 1 to 4 carbon atoms and $R^3$ represents a hydrogen atom or an alkyl group having from 1 to 10 carbon atoms.

11. Compounds as claimed in claim 1, wherein n is 0.

12. Compounds as claimed in claim 1, wherein:
$R^1$ represents an alkyl group having from 1 to 4 carbon atoms or an allyl group;
$R^2$ represents an alkyl group having from 1 to 4 carbon atoms;
$R^3$ represents a hydrogen atom or an alkyl group having from 1 to 10 carbon atoms;
X represents an ethylene group; and
n is 0.

13. Compounds as claimed in claim 1, selected from the group consisting of:
4-{N-methyl-N-[2-(2-methylphenoxy)ethyl]amino}quinazoline;
4-{N-[2-(2-methylphenoxy)ethyl]-N-propylamino}quinazoline;
4-{N-allyl-N-[2-(2-methylphenoxy)ethyl]amino}quinazoline; and
4-{N-[2-(4-chloro-2-methylphenoxy)ethyl]-N-methylamino}quinazoline.

14. Compounds as claimed in claim 1, selected from the group consisting of:
4-{N-[2-(2-isopropylphenoxy)ethyl]-N-methylamino}quinazoline;
4-{N-[2-(2,4-dimethylphenoxy)ethyl]-N-methylamino}quinazoline; and
4-{N-[2-(5-isopropyl-2-methylphenoxy)ethyl]-N-methylamino}quinazoline.

15. Compounds as claimed in claim 1, selected from the group consisting of
4-{N-[2-(2-isopropylphenoxy)ethyl]-N-propylamino}quinazoline;
4-{N-allyl-N-[2-(2-isopropylphenoxy)ethyl]amino}quinazoline;
4-{N-allyl-N-[2-(2,4-dimethylphenoxy)ethyl]amino}quinazoline;
4-{N-butyl-N-[2-(2-isopropylphenoxy)ethyl]amino}quinazoline;
4-{N-[2-(2-isopropylphenoxy)ethyl]-N-methylamino}quinazoline oxalate;

4-{N-[2-(4-hexyl-2-methylphenoxy)ethyl]-N-methylamino}quinazoline; and

4-{N-methyl-N-[2-(2-methyl-4-octylphenoxy)ethyl]amino}quinazoline.

16. An agricultural or horticultural preparation comprising, as active ingredient, a compound of formula (I):

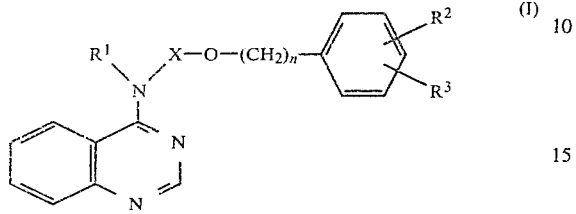

(wherein:

$R^1$ represents an alkyl group, a cycloalkyl group, an alkenyl group or a benzyl group;

$R^2$ and $R^3$ are the same or different and each represents a hydrogen atom, an alkyl group, an alkoxy group or a halogen atom;

X represents an alkylene group; and n represents 0 or 1)

or a salt or hydrate thereof, in admixture with an agriculturally or horiculturally acceptable carrier or diluent.

17. A preparation as claimed in claim 16, wherein:

$R^1$ represents an alkyl group having from 1 to 10 carbon atoms, a cycloalkyl group having from 5 to 7 carbon atoms, an alkenyl group having from 3 to 6 carbon atoms or a benzyl group;

$R^2$ and $R^3$ are the same or different and each represents a hydrogen atom, an alkyl group having from 1 to 10 carbon atoms, an alkoxy group having from 1 to 4 carbon atoms or a halogen atom;

X represents an alkylene group having from 1 to 8 carbon atoms; and n is 0 or 1.

18. A preparation as claimed in claim 16, wherein:

$R^1$ represents an alkyl group having from 1 to 4 carbon atoms or an allyl group;

$R^2$ represents an alkyl group having from 1 to 4 carbon atoms;

$R^3$ represents a hydrogen atom or an alkyl group having from 1 to 10 carbon atoms;

X represents an ethylene group; and n is 0.

19. A preparation as claimed in claim 16, wherein said compound is selected from the group consisting of:

4-{N-methyl-N-[2-(2-methylphenoxy)ethyl]amino}quinazoline;

4-{N-[2-(2-methylphenoxy)ethyl]-N-propylamino}quinazoline;

4-{N-allyl-N-[2-(2-methylphenoxy)ethyl]amino}quinazoline; and

4-{N-[2-(4-chloro-2-methylphenoxy)ethyl]-N-methylamino}quinazoline.

20. A preparation as claimed in claim 16, wherein said compound is selected from the group consisting of:

4-{N-[2-(2-isopropylphenoxy)ethyl]-N-methylamino}quinazoline;

4-{N-[2-(2,4-dimethylphenoxy)ethyl]-N-methylamino}quinazoline; and

4-{N-[2-(5-isopropyl-2-methylphenoxy)ethyl]-N-methylamino}quinazoline.

21. A preparation as claimed in claim 16, wherein said compound is selected from the group consisting of:

4-{N-[2-(2-isopropylphenoxy)ethyl]-N-propylamino}quinazoline;

4-{[N-allyl-N-[2-(2-isopropylphenoxy)ethyl]amino}quinazoline;

4-{N-allyl-N-[2-(2,4-dimethylphenoxy)ethyl]amino}quinazoline;

4-{N-butyl-N-[2-(2-isopropylphenoxy)ethyl]amino}quinazoline;

4-{N-[2-(2-isopropylphenoxy)ethyl-N-methylamino}quinazoline oxalate;

4-{N-[2-(4-hexyl-2-methylphenoxy)ethyl]-N-methylamino}quinazoline; and

4-{N-methyl-N-[2-(2-methyl-4-octylphenoxy)ethyl]amino}quinazoline.

22. A method of protecting growing plants and/or seeds against bacterial, fungal, insect or mite attack by applying to the seeds, plants or soil a compound of formula (I):

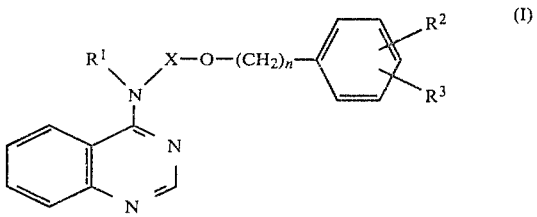

(wherein:

$R^1$ represents an alkyl group, a cycloalkyl group, an alkenyl group or a benzyl group;

$R^2$ and $R^3$ are the same or different and each represents a hydrogen atom, an alkyl group, an alkoxy group or a halogen atom;

X represents an alkylene group; and n represents 0 or 1)

or a salt or hydrate thereof.

23. A method as claimed in claim 22, wherein:

$R^1$ represents an alkyl group having from 1 to 10 carbon atoms, a cycloalkyl group having from 5 to 7 carbon atoms, an alkenyl group having from 3 to 6 carbon atoms or a benzyl group;

$R^2$ and $R^3$ are the same or different and each represents a hydrogen atom, an alkyl group having from 1 to 10 carbon atoms, an alkoxy group having from 1 to 4 carbon atoms or a halogen atom;

X represents an alkylene group having from 1 to 8 carbon atoms; and n is 0 or 1.

24. A method as claimed in claim 22, wherein:

$R^1$ represents an alkyl group having from 1 to 4 carbon atoms or an allyl group;

$R^2$ represents an alkyl group having from 1 to 4 carbon atoms;

$R^3$ represents a hydrogen atom or an alkyl group having from 1 to 10 carbon atoms;

X represents an ethylene group; and n is 0.

25. A method as claimed in claim 22, wherein: said compound is selected from the group consisting of:

4-{N-methyl-N-[2-(2-methylphenoxy)ethyl]amino}quinazoline;

4-{N-[2-(2-methylphenoxy)ethyl]-N-propylamino}quinazoline;

4-{N-allyl-N-[2-(2-methylphenoxy)ethyl]amino}-quinazoline; and

4-{N-[2-(4-chloro-2-methylphenoxy)ethyl]-N-methylamino}quinazoline.

26. A method as claimed in claim 22, wherein: said compound is selected from the group consisting of:

4-{N-[2-(2-isopropylphenoxy)ethyl]-N-methylamino}quinazoline;

4-{N-[2-(2,4-dimethylphenoxy)ethyl]-N-methylamino}quinazoline; and

4-{N-[2-(5-isopropyl-2-methylphenoxy)ethyl]-N-methylamino}quinazoline.

27. A method as claimed in claim 22, wherein: said compound is selected from the group consisting of 4-{N-[2-(2-isopropylphenoxy)ethyl]-N-propylamino}quinazoline;

4-{N-allyl-N-[2-(2-isopropylphenoxy)ethyl]amino}-quinazoline;

4-{N-allyl-N-[2-(2,4-dimethylphenoxy)ethyl]amino}-quinazoline;

4-{N-butyl-N-[2-(2-isopropylphenoxy)ethyl]amino}-quinazoline;

4-{N-[2-(2-isopropylphenoxy)ethyl]-N-methylamino}quinazoline oxalate;

4-{N-[2-(4-hexyl-2-methylphenoxy)ethyl]-N-methylamino}quinazoline; and

4-{N-methyl-N-[2-(2-methyl-4-octylphenoxy)ethyl]amino}quinazoline.

* * * * *